(12) United States Patent
Marsh

(10) Patent No.: US 6,855,928 B2
(45) Date of Patent: Feb. 15, 2005

(54) ANALYSIS OF SEMICONDUCTOR SURFACES BY SECONDARY ION MASS SPECTROMETRY AND METHODS

(75) Inventor: Eugene P. Marsh, Boise, ID (US)

(73) Assignee: Micron Technology, Inc., Boise, ID (US)

(*) Notice: Subject to any disclaimer, the term of this patent is extended or adjusted under 35 U.S.C. 154(b) by 159 days.

(21) Appl. No.: 10/358,939

(22) Filed: Feb. 4, 2003

(65) Prior Publication Data

US 2003/0136906 A1 Jul. 24, 2003

Related U.S. Application Data

(63) Continuation of application No. 09/795,999, filed on Feb. 28, 2001, now Pat. No. 6,528,786, which is a continuation of application No. 09/309,208, filed on May 10, 1999, now Pat. No. 6,232,600, which is a continuation of application No. 09/035,197, filed on Mar. 5, 1998, now Pat. No. 5,920,068.

(51) Int. Cl.[7] ............................................. H01J 37/26
(52) U.S. Cl. ....................... 250/309; 250/281; 250/282; 250/287
(58) Field of Search ................................. 250/309, 307, 250/306, 281, 282, 287

(56) References Cited

U.S. PATENT DOCUMENTS

| | | |
|---|---|---|
| 4,611,120 A | 9/1986 | Bancroft et al. |
| 4,874,946 A | 10/1989 | Kazmerski |
| 4,912,325 A | 3/1990 | Vandervorst et al. |
| 5,087,815 A | 2/1992 | Schultz et al. |
| 5,252,361 A | 10/1993 | Frechette et al. |
| 5,332,879 A | 7/1994 | Radhakrishnan et al. |
| 5,442,174 A | 8/1995 | Kataoka et al. |
| 5,502,305 A | 3/1996 | Kataoka |
| 5,521,377 A | 5/1996 | Kataoka et al. |
| 5,689,112 A | 11/1997 | Enge et al. |
| 5,714,757 A | 2/1998 | Itabashi et al. |
| 5,835,225 A | 11/1998 | Thakur |
| 5,920,068 A * | 7/1999 | Marsh .......................... 250/309 |
| 6,008,491 A | 12/1999 | Smentkowski et al. |
| 6,232,600 B1 * | 5/2001 | Marsh .......................... 250/309 |
| 6,271,519 B1 | 8/2001 | Marsh |
| 6,528,786 B2 * | 3/2003 | Marsh .......................... 250/309 |

OTHER PUBLICATIONS

Louis Denes, *The Effect of Wafer Flatness on Yield by Off-Line Computer Simulation of the Photolithographic Process*; Semiconductor Processing, ASTM STP 850, American Society for Testing and Materials, 1984; pps. 143–159.

* cited by examiner

Primary Examiner—Kiet T. Nguyen
(74) Attorney, Agent, or Firm—TraskBritt

(57) ABSTRACT

An apparatus and method for mass spectrometric determination of contaminant components of a thin oxide surface layer of a semiconductor wafer using a movable mechanical stage to scan and raster a large area of the wafer in a continuous scanning motion. The mass of analyte is greatly increased, resulting in improved sensitivity to trace components in the surface layer by a factor of 10–100 or more. A light beam interferometer is used to determine non-planarity from e.g. warping of the wafer and provide a correction by maintaining a constant separation between the wafer and the extraction plate or adjusting the electrical bias of the wafer relative to the extraction bias.

20 Claims, 8 Drawing Sheets

TABLE 1 -- Wafer surfaces which have been measured by grazing incidence interferometers

| Substrate Materials | Surface Conditions |
|---|---|
| Silicon | |
| Silicon on Sapphire | |
| GaAs | |
| Sapphire | |
| G. G. G. | |
| | Oxides |
| | Nitrides |
| | Aluminized |
| | Epitaxial |
| | Silicides |
| | Polysilicon |
| | Lapped |
| | Etched |
| | Sawn |
| | Patterned |

*Fig. 8*

ANALYSIS OF SEMICONDUCTOR SURFACES BY SECONDARY ION MASS SPECTROMETRY AND METHODS

CROSS-REFERENCE TO RELATED APPLICATIONS

This application is a continuation of application Ser. No. 09/795,999, filed Feb. 28, 2001, now U.S. Pat. No. 6,528,386, issued Mar. 4, 2003, which is a continuation of application Ser. No. 09/309,208, filed May 10, 1999, now U.S. Pat. No. 6,232,600, issued May 15, 2001, which is a continuation of application Ser. No. 09/035,197, filed Mar. 5, 1998, now U.S. Pat. No. 5,920,068, issued Jul. 6, 1999.

BACKGROUND OF THE INVENTION

1. Field of the Invention

This invention relates generally to the bulk measurement of trace contaminants in the surface layers of semiconductor wafers and dice, as well as material composition as a function of depth. More particularly, the invention pertains to improvements in methods and apparatus for mass spectrographic analysis of wafer and semiconductor die surface layers.

2. State of the Art

Secondary ion mass spectrometry (SIMS) is known as a method for determining particular constituents of a semiconductor material and providing a quantitative measurement of each.

Generally, this method involves bombarding a sample with "primary" ions, e.g., oxygen ions, measuring the intensities of secondary ions emitted or sputtered from the sample, and calculating the quantity of each conductive impurity based on the secondary emission as compared to the emission of standard materials. The sputtering and analysis is typically conducted in an ultra-high-vacuum environment.

SIMS may be used to achieve parts-per-billion (ppb) detection limits for bulk analysis and for determining material composition as a function of depth, provided the sample size is sufficiently large. The extreme sensitivity of SIMS results from its ability to "consume" large amounts of sample material, and thus process a large number of atoms to detect. However, because of the high rate of material consumption from a very small sample, dynamic SIMS is generally not appropriate for analysis of a very thin oxide surface layer of a semiconductor die and plurality of semiconductor dice in wafer form. Typical semiconductor contaminants may include lithium, boron, sodium, potassium, iron, sulfur, and carbon, all of which are found in the oxide layer on the semiconductor die surface. For the case of surface contaminants on silicon, the oxide layer is generally not more than about 15 Å thick. However, several minutes are required to obtain a sufficient number of data points at the required analyte masses, so the method is not useful for this application as the oxide layer will be quickly consumed.

It is desirable to be able to detect the concentrations of boron, lithium and sodium to less than about $1 \times 10^6$ atoms per square centimeter of semiconductor die surface area. These detection limits are considerably lower than currently obtainable.

U.S. Pat. No. 4,874,946 of Kazmerski discloses a method and apparatus for mapping the chemical composition of a solid device, using a rasterable SIMS mass analyzer.

U.S. Pat. No. 4,611,120 of Bancroft et al. discloses a method for suppressing molecular ions in the secondary ion mass spectra of a commercial SIMS instrument.

U.S. Pat. No. 5,521,377 of Kataoka et al. discloses a method for analysis of a solid in a planar or depth-wise direction using sputtering with two ionizing beams and detecting a two-atom composite ion.

U.S. Pat. No. 5,502,305 of Kataoka and U.S. Pat. No. 5,442,174 of Kataoka et al. disclose methods for analysis of a solid in a planar or depth-wise direction using sputtering with an ionizing beam and detecting a three-atom composite ion.

U.S. Pat. No. 5,332,879 of Radhakrishnan et al. discloses the use of a pulsed laser beam to remove contaminant metals from the surface of a polyimide layer. The disclosure indicated high surface metal removal with "minimal" removal of the polyimide, i.e., 250–500 Å per pulse. Such ablation rates are far greater than useful in the analysis of surface contaminants in semiconductor devices, where the surface oxide layer is typically only about 15 Å in depth.

Time-of-flight secondary ion mass spectroscopy (TOF-SIMS) has also been found useful for bulk analysis of materials, provided the sample size is sufficiently large. The TOF-SIMS instrument directly measures the speeds of secondary ions by measuring the time taken to travel a given distance. Knowing the ion's energy, which is defined by the spectrometer's acceleration voltage, its mass can then be calculated. Typically, the time intervals are defined as the difference in time between pulsing the ion gun and the ion arrival at the detector. The mass range is then calibrated using at least three known mass peaks.

TOF-SIMS instruments have been found to provide some of the lowest detection limits in surface analysis, typically even lower than total reflection X-ray fluorescence (TXRF) with vapor phase decomposition (VPD). For the TOF-SIMS instrument, some representative detection limits are $<1\times10^8$ atoms/cm$^2$ for lithium, boron and sodium, and $<1\times10^9$ atoms/cm$^2$ for iron.

The TXRF instrument, on the other hand, is incapable of detecting elements lighter than sulfur, so critical elements such as sodium, carbon, lithium and boron cannot be detected.

Thus, the TOF-SIMS method would appear to be potentially useful for surface analysis, but instrumental constraints limit the sampling area to about 100×100 µm, and sampling of a relatively shallow oxide layer over the 100× 100 µm area does not produce sufficient sample material for achieving the desired detection limits.

For TOF-SIMS, the detection limits are determined by the transmission and exceptance of the mass spectrometer, the sputter and ionization yield of the analyte, and the amount of material consumed during the analysis. These parameters may be categorized as the useful yield of the mass spectrometer and volume of analyte. Sampling of the maximum raster area of 100×100 µm to a depth of about 13 Å will produce about $3\times10^{11}$ particles. This is equivalent to between 0.3 to 30 (thirty) counts of a measured component at the 1 ppm level depending upon the ionization yields. It is critical to semiconductor device manufacture that bulk concentrations of some contaminants as low as 0.01 ppm and even 1 ppb be accurately detectable. Thus, current detection limits for certain contaminants must be reduced by a factor on the order of about 100 more.

U.S. Pat. No. 5,087,815 of Schultz et al. discloses a method and apparatus for a TOF-SIMS isotopic ratio determination of elements on a surface.

BRIEF SUMMARY OF THE INVENTION

The present invention provides a method for substantially increasing the sensitivity of a mass spectrographic analytical method for determining contaminant levels in the surface oxide layer of a semiconductor die or semiconductor dice in wafer form.

The present invention further provides a method for increasing the sensitivity of surface contaminant analysis of an oxide layer of a wafer by secondary ion mass spectroscopy (SIMS).

The present invention additionally provides a method for increasing the sensitivity of surface contaminant analysis by time-of-flight secondary ion mass spectroscopy (TOF-SIMS).

Related to the present invention is providing a method for determining the bulk concentration of contaminants in a surface oxide layer of a semiconductor material by SIMS or TOF-SIMS, wherein the surface area which may be sampled may be much greater than the electrostatic raster limits of the sputtering primary beam, and/or acceptance area limits of the spectrometer.

The present invention further includes apparatus for achieving the desired rastered sputtering and analysis of an enlarged area of a semiconductor wafer.

The present invention includes a method and means which enable sputtering to a uniform sampling depth and maintaining mass resolution irrespective of warpage or other non-planarity of a wafer. Thus, contaminant analysis of semiconductor wafers and semiconductor dice by SIMS or TOF-SIMS may be limited to the surface oxide layer. Additionally, advantages and novel features of this invention are set forth in part in the description infra. These advantages and features will become apparent to those skilled in the art upon examination of the following specification and drawings, or may be learned by practice of the invention. The various combinations of apparatus and/or methods which comprise the invention are pointed out in the appended claims.

In accordance with this disclosure, a first aspect of the invention comprises the steps of:

(a) scan-sputtering a large area of a semiconductor wafer surface while continuously moving, i.e., scanning the wafer with a supporting mechanical stage in a first direction, and mechanically rastering the wafer in a second direction, whereby the scanning speed is controlled to limit the sputtering to a sampling depth not generally exceeding the depth Q of the surface oxide layer, and the rate of sputtered secondary ionic emission directed to the SIMS detector simultaneously satisfies the SIMS consumption rate; the total sputtered area is generally at about $10^4$ $\mu m^2$ for a surface oxide layer sputtered to a depth of about 15 Å;

(b) directing a stream of secondary ions produced by the primary ionizing beam into a SIMS for mass spectrographic analysis at a rate satisfying the SIMS sample consumption rate for a time period sufficient for high analytical sensitivity; and (c) computing the total mass of each of the selected detected ions.

In a second aspect of the invention, a combination of mechanical scanning/rastering and primary beam electrostatic rastering is used to move the sputtering and sampling operations over the wafer surface at a speed responsive to a controlled sampling depth and sample consumption over a large area.

In a third aspect of the invention, mechanical scanning and rastering are used to sample a large area of a semiconductor material with a continuous sputtering and analysis by a time-of-flight secondary ion mass spectrometer (TOF-SIMS).

In a fourth aspect of the invention, a combination of mechanical rastering and primary beam rastering, e.g., electrostatic rastering is applied to a time-of-flight secondary ion mass spectometer (TOF-SIMS) whereby a large area of controlled limited depth may be sputtered at a speed which simultaneously (a) limits total sputtering depth generally to the surface oxide layer and (b) provides a large quantity of secondary ions for high resolution of measured atoms.

In one preferred method, an area, typically limited by the electrostatic rastering capability TOF-SIMS instrument to about 100 $\mu m^2$, is repetitively sputtered and analyzed. The primary beam is then moved to a new area by mechanical stage rastering, and the new area is repetitively sputtered and analyzed using electrostatic rastering. The process is repeated until sufficient sample material is consumed for each "slice" the surface oxide layer to provide the desired detection limits. The total area sampled is limited only by the total area of the wafer or die being analyzed, and the time available for analysis.

Thus, the detection limits are reduced to low levels. For example, the detection limits of lithium, boron, and sodium may be extended to less than about $1 \times 10^6$ atoms/cm$^2$.

The detection limits of trace iron may be at somewhat higher concentrations because of the peak shape of the neighboring SiO$_2$.

In a variant of the above method, mechanical rastering is performed such that a thin slice of an enlarged area, e.g., 400–1600 $\mu m^2$ is sputtered and analyzed before the next slice is sputtered and analyzed.

In each of the embodiments described and illustrated of the present invention, it should be kept in mind that removal of the surface layer by sputtering is conducted in a continuous scanning motion rather than by stepping along a series of stationary raster points. The sputter depth is controlled by the scanning speed, and the sputter rate (mass per unit time) is controlled by the ion gun characteristics.

Because of the much greater area which is rastered, sputtered and analyzed, the analysis is more sensitive to non-planarity, e.g., warpage, of the wafer. Non-uniform extraction fields and some loss of mass resolution inaccuracy in analysis may result. This would have adverse effects on detection limits of Fe since the neighboring peak of Si$_2$ is at the same nominal mass as Fe and will overlap Fe without sufficient mass resolution.

Thus, in another aspect of the present invention, a method and apparatus are provided for counteracting the effects of wafer warpage (non-planarity) upon analytical results. In accordance with the invention, a non-invasive laser interferometer is incorporated into the SIMS or TOF-SIMS spectrometer to measure non-planarity as a function of wafer location, and permit correction of the stage elevation or the sample electrical potential relative to the extraction potential. The sample elevation measurements may be made prior to the mass spectrometric analysis and then used to control e.g. the stage elevation during rastering/sputtering, or the sample elevation measurements may be made during the rastering/sputtering operation for continuous in situ correction. Because of the required physical separation, e.g. about 1–3 cm., of the sputter beam and the interferometer laser beam in the latter case, the sample surface elevation at the sputter location may be calculated and correction made therefor by a computer program of the process controller, based on distant measurements and assuming a particular warpage shape. Alternatively, the wafer may be first scanned by the interferometer and the data may be stored and used to provide correction during the sputtering/analyzing operation.

BRIEF DESCRIPTION OF THE SEVERAL VIEWS OF THE DRAWINGS

The invention is illustrated in the following figures, wherein the elements are not necessarily shown to scale.

FIG. 8 is a table of wafer surfaces capable of measurement by a grazing incidence interferometer.

DETAILED DESCRIPTION OF THE INVENTION

Figure 1:
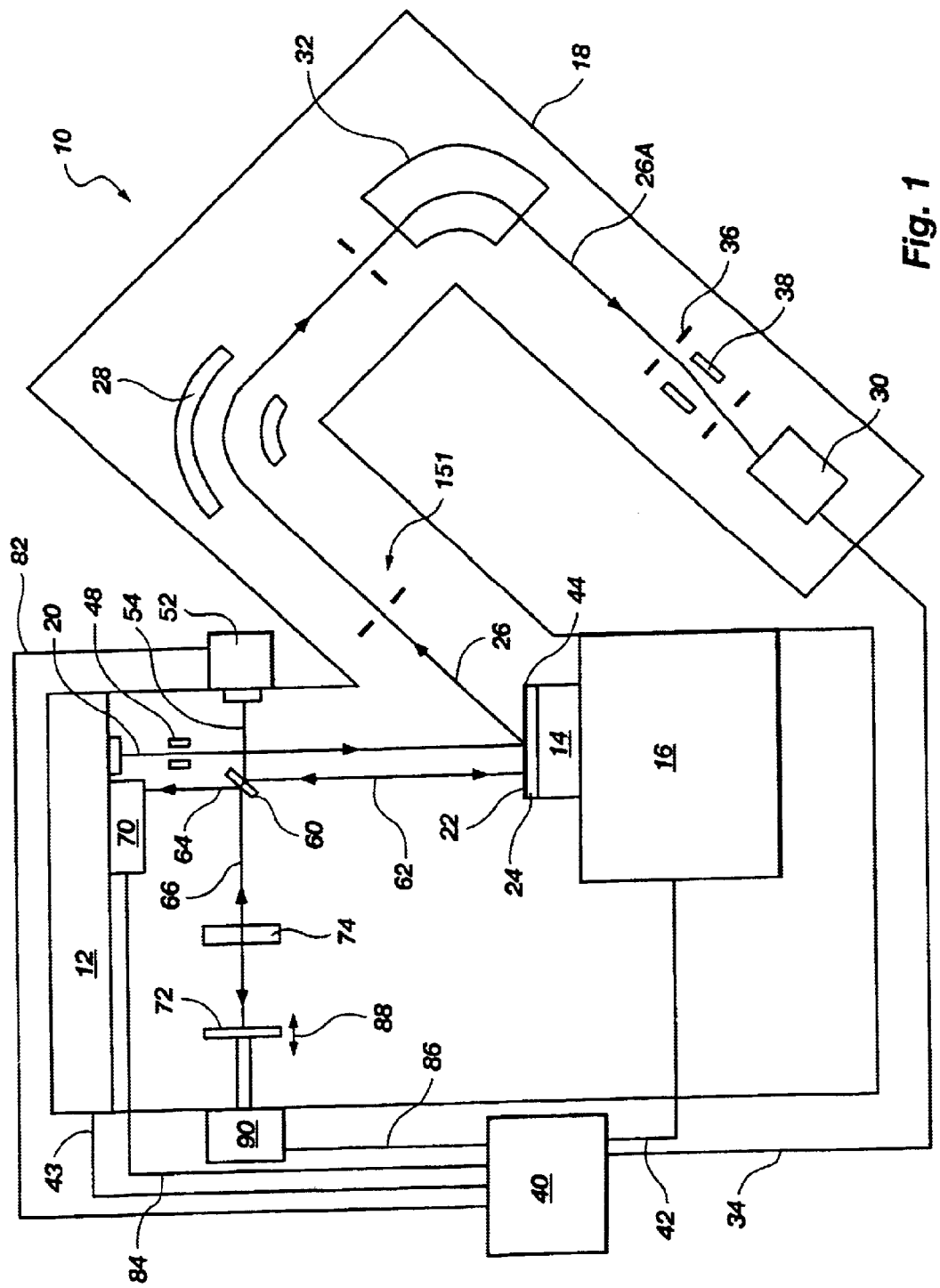
FIG. 1 front diagrammatic view of an exemplary secondary ion mass spectometer (SIMS) apparatus of the invention for high resolution detection of component concentrations in a thin surface oxide layer of a semiconductor die or wafer.

With reference to the drawings of FIGS. 1–4, and particularly to drawing FIG. 1, a secondary ion mass spectrometer (SIMS) analysis system 10 of the present invention is illustrated. The SIMS analysis system 10 includes a primary sputtering ion generator or ion gun 12, a sample stage 14 having a stage controller 16, and a secondary ion analyzer 18. A primary ion beam 20 is directed from the primary sputtering ion generator or ion gun 12 onto the surface 22 of a semiconductor die or wafer 24 mounted on the stage 14, and a stream of secondary ions, represented by line 26, is sputtered from the die 24 by the primary ion beam 20, extracted by the extraction field between the wafer 24 and the extraction plate 151 and directed through an electric field 28 and a magnetic field 32 for separation of ions, i.e. resolution of the ion stream. The stream 26A of partially resolved secondary ions is then directed through a collector slit 36 and deflection electrode 38 to a spectrometric detector 30. The detector 30 is conformed to detect the resolved secondary ionic emission stream 26A and relay measured values via signal conductor 34 to a controller/analyzer/recorder 40. Other time-dependent inputs to the controller/analyzer/recorder 40 include an indication of the sampling location from the stage controller 16 via conductor 42. The controller/analyzer/recorder 40 controls the ion gun 12 via signal conduit 43.

The controller/analyzer/recorder 40 receives the measured values of current measurements from signal conductor 34, determines the particular secondary ions thereof, and sums the counts to provide a "bulk" concentration of each ion, and/or a concentration of each as a function of X-Y location and/or an interval of depth Z in the wafer or die 24. In accordance with the method of the invention as generally practiced, the wafer or die 24 has a surface oxide layer 44 in which are the contaminant atoms/molecules of interest, and the depth of sputtering does not generally exceed the depth 46 (FIG. 2) of the surface oxide layer.

As used herein, the term "mastering" refers to the movement of a primary ion beam, laser light beam, or other apparatus or process in a line over the surface of a wafer or other planar material, and lateral movement, in turn, to each of a plurality of subsequent lines, whereby a significant area of the surface is subjected to the apparatus or process of the present invention.

The functions of the controller/analyzer/recorder 40 need not be confined to a single instrument, but may be distributed, for example, in the ion gun 12, stage controller 16, spectrometric detector 30, and/or controller/analyzer/recorder 40.

The primary ion beam 20 may be a stream of e.g., $O_2^+$ ions, $Cs^+$ ions, or other ions, as known in the art. As also known in the art, the primary ion beam 20 may be laterally focusable by an electrostatic lens 48 to incrementally raster the ionization of the wafer surface 22. The maximum area of the wafer surface 22 which is electrostatically rasterable under the constraints of currently available SIMS equipment has dimensions of about 100×100 $\mu$m. In some configurations of the present invention, the primary ion beam is not rastered.

In one aspect of the invention, a movable stage 14 with a stage controller 16 is provided to support the wafer or die 24 and to provide both a controllable scanning motion in a first direction and a rastering motion of the wafer or die in a second direction. The stage 14 is preferably movable in the lateral X and Y axes at a controllable variable speed, such as between about 200 and 1000 $\mu$m/sec., and is movable along the Z axis. The surface area which may be sampled is thus not limited by the electrostatic beam-raster.

In another aspect of the present invention, a movable stage 14 with a stage controller 16 is provided to support the die or wafer 24 and to provide a controllable scanning and raster pattern in combination with the electrostatic rastering of the electrostatic lens 48, greatly increasing the total rasterable area thereby.

Figure 2:
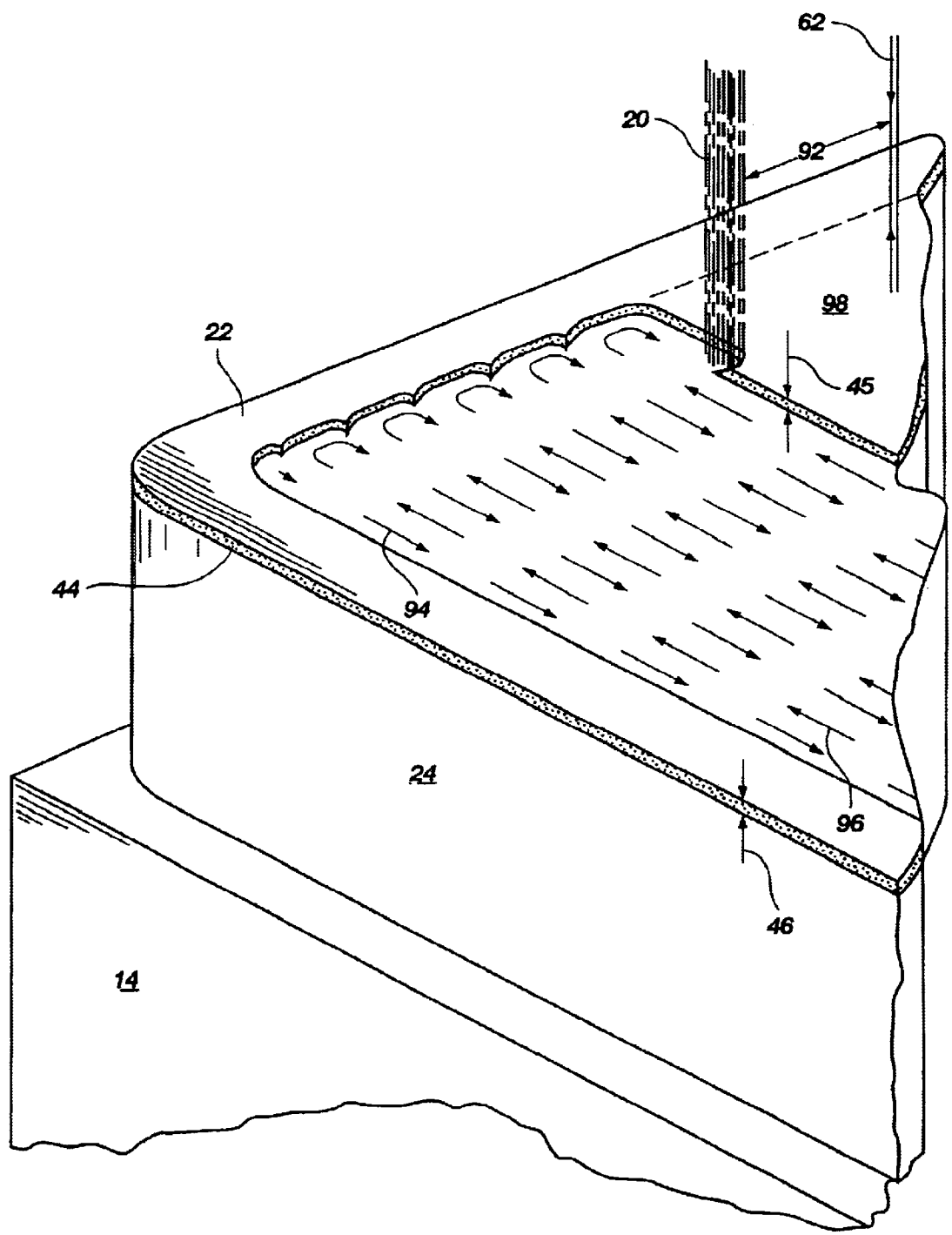
FIG. 2 is a perspective view of a portion of a semiconductor wafer illustrating a method of the invention for determining the component concentrations in the surface oxide layer thereof.

In drawing FIGS. 1 and 2, stage 14 is an automated sample stage which permits e.g., scanning and rastering of wafers of any size typically used in the industry, such as 8 inches (20.3 cm.) in diameter. The wafer surface 22 is sputtered by primary ion beam 20 while scanning at a rate whereby the total sputtering depth does not generally exceed the depth 46 of the surface oxide layer 44 on the wafer surface. Thus, a bulk analysis at lower concentration limits may be obtained for the surface oxide layer 44.

An example of a raster pattern is shown in drawing FIG. 2 wherein straight-line scanning along line or path 94 is followed by rastering to the adjacent line 96 and reversing the scanning direction. This is repeated across the surface 22 until the entire area to be sampled is sputtered to the control depth 45 and analyzed.

If desired, the scanning may be at a speed and/or primary beam strength whereby only a fraction of the surface oxide layer 44 is removed and analyzed per pass. Thus, a bulk analysis of the trace components may be obtained which will have limits equal to or lower than conventional bulk analyses.

For determination of composition as a depth function, the wafer surface 22 is repeatedly and progressively scanned in multiple passes, and the secondary ion stream from each pass is analyzed and correlated as a function of X-Y position and depth (Z position).

Electrostatic beam rastering may be added to a mechanical scanning/rastering. In this configuration, a beam rasterable area is scan-sputtered (as opposed to point-sputtered).

Control of the rastering and scanning motions is combined whereby a much larger surface area may be scanned and rastered.

Figure 4:
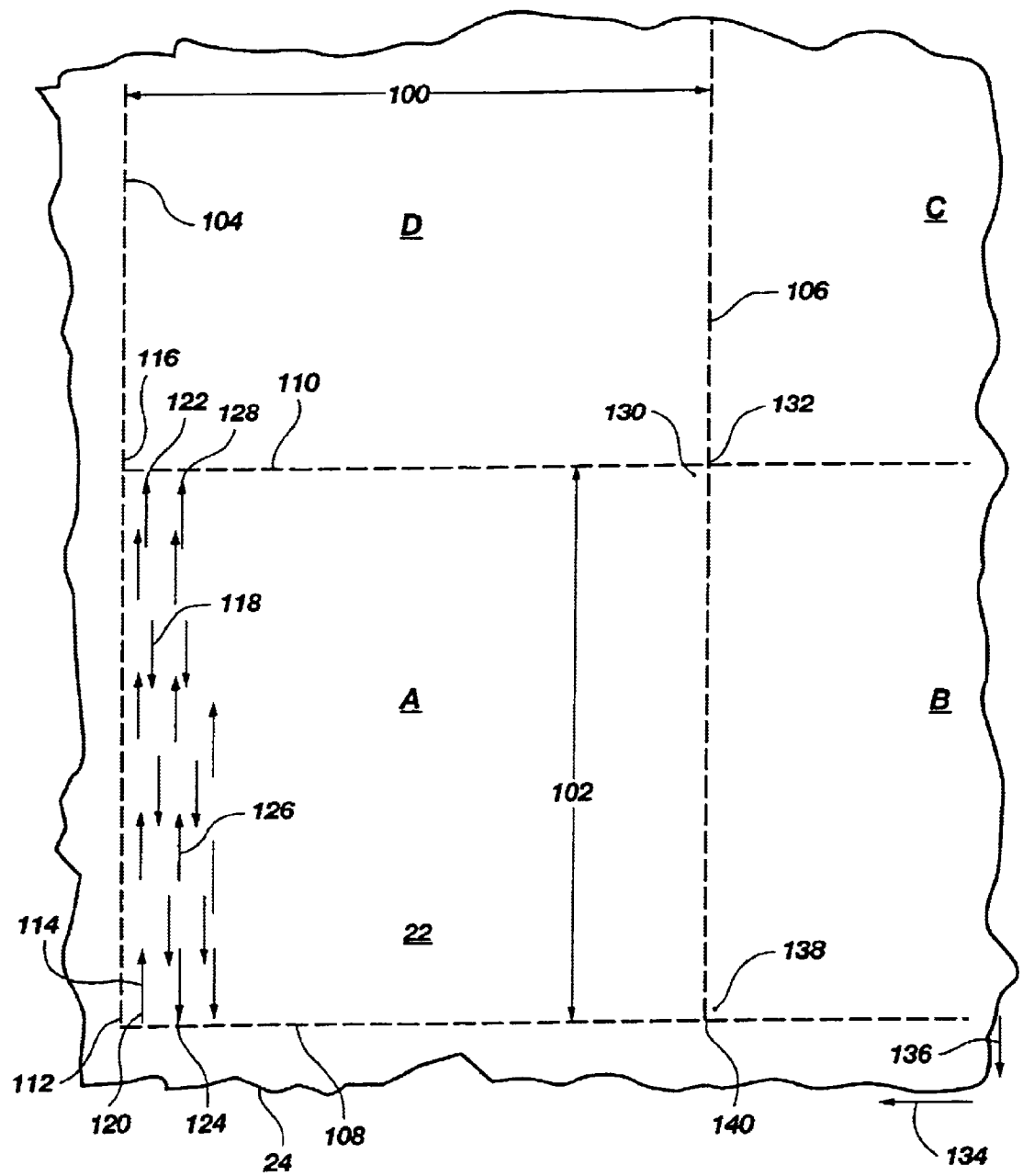
FIG. 4 is a plan view of a portion of a semiconductor wafer, illustrating an exemplary scanning/rastering pattern of the invention.

As shown in drawing FIG. 4, a surface 22 of a wafer 24 is sputter-sampled and analyzed by an apparatus of the present invention. Sector A comprises the maximum area electrostatically rasterable by the ion gun 12 and is shown as a square pattern having dimensions 100 and 102 of e.g., 100 μm×100 μm. Sector A is bounded by lines 104, 106, 108 and 110. Adjacent sectors B, C, and D are shown in part, each having dimensions equal to sector A.

The exemplary raster pattern of the ion beam starts at point 120 adjacent corner 112, and progresses along line or path 114 to point 122 adjacent corner 116. At that location, the beam is rastered along line 118 to point 124, and sputtering continues along line 126 to point 128. The ion beam 20 is continuously moved at a speed and primary beam strength sufficient to remove and ionize the surface 22 to the desired depth. The secondary ion stream 26 is directed into the secondary ion analyzer 18. The scanning and rastering of the primary ion beam 20 is continued over the entire sector A to point 130 adjacent corner 132.

The wafer 24 is then mechanically rastered by the movable sample stage 14 in direction 134 so that sector B occupies the area previously occupied by sector A. At the same time, the primary ion beam 20 is moved in directions 134 and 136 to focus on point 138 adjacent corner 140, and begin a scanning, sampling and analysis of sector B. These operations may be continued for any number of sectors, limited only by the size of the wafer 24 and the time available for the analysis.

Thus, for example, a first analysis area of 200×200 μm may be scanned at a speed to complete sputtering in 0.5 second. The analysis depth will be about 13 Å which is close to the depth of the surface layer. A 300 nA primary probe beam will consume the sputtered mass (about $3\times10^{11}$ particles) from this sputtered area ($4\times10^4$ μm$^2$) in about 0.5 seconds, and yield accurate bulk analyses of contaminants at low concentration levels. Following sputtering of this 200×200 μm area, the wafer is moved, i.e., rastered, by the mechanical stage to a second area, typically of equal size and adjacent the first area, which is then scanned. A plurality of e.g., 100 more areas may be thus sampled and analyzed, depending upon the wafer size, greatly increasing the sensitivity to contaminant levels. As described above, the primary ion beam electrostatic raster is not used; all movement is controlled by the mechanical stage.

Alternatively, the electrostatic rastering and mechanical rastering devices may be combined to provide a linear scanning motion for continuous sputtering and a raster step motion for moving the primary ion beam 20 to a new line of sputtering. A single pass, for bulk analysis, or multiple passes for depth analysis, may be performed.

Other raster patterns may be used, and the number of sectors chosen to raster by this method may be any convenient number which provides the desired analytical accuracy.

Consumption of the substrate underlying the surface oxide layer 44 is avoided, increasing the concentrations of contaminant ions to be measured and reducing the analytical limits by a factor of about 10 to 100 or even more. Thus, surface analysis may be achieved with the same sensitivity as a typical SIMS bulk analysis.

For surface analysis of large areas such as on a wafer of 8 inches or greater diameter, any surface non-planarity resulting from e.g., warping, will affect the extraction voltage, and hinder mass resolution and thus abundance sensitivity. Such warpage on an 8 inch wafer is typically specified to be less than about 40 μm across the wafer. Thus, the allowable non-planarity would yield up to a 2% change in extraction field for extraction gate. Unless corrected, the resulting error may cause an unacceptable loss in mass resolution and abundance sensitivity.

Thus, in a further feature of the invention, an interferometry apparatus and method are combined with compensation apparatus and methods for counteracting sample non-planarity.

Figure 3:
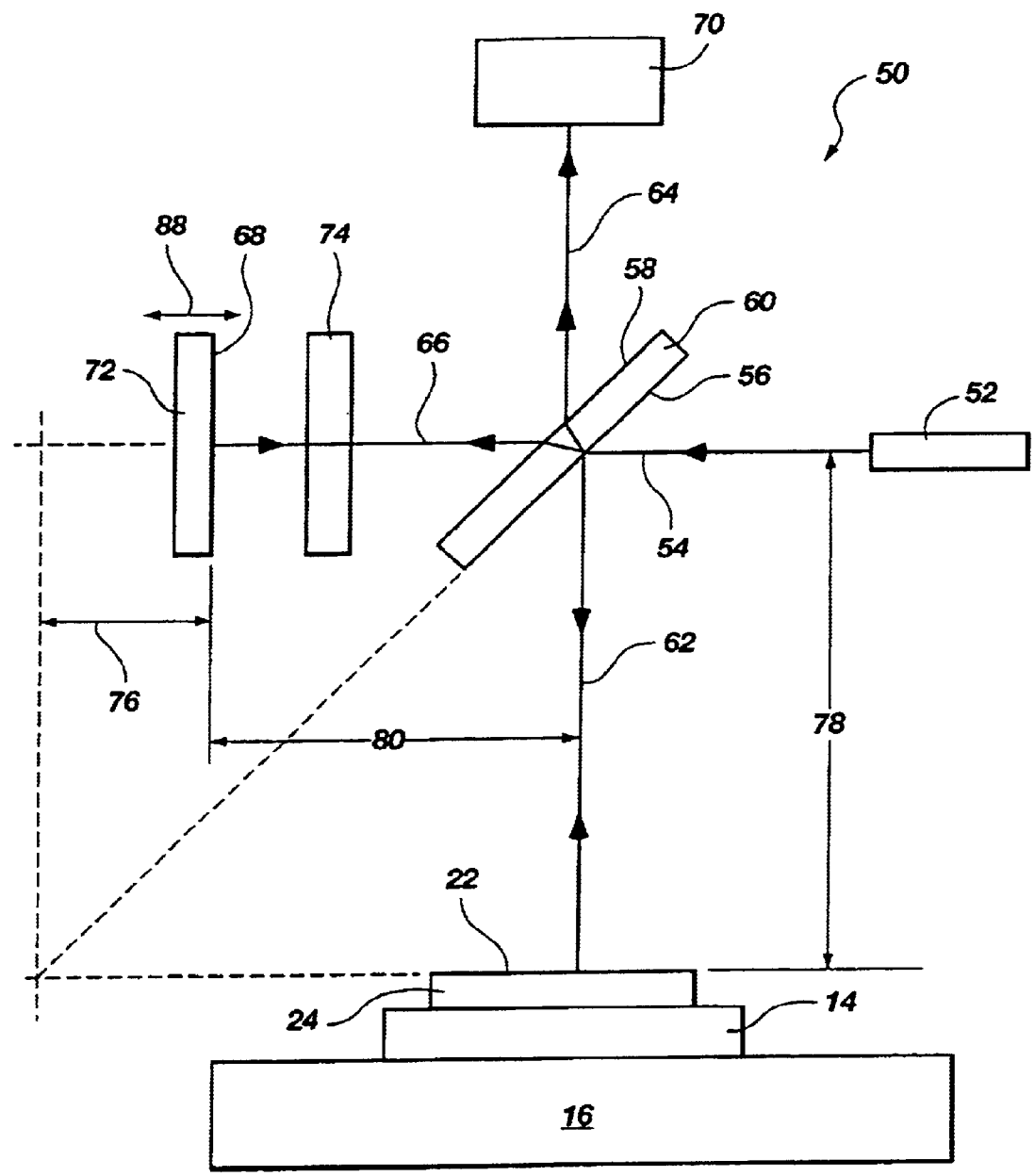
FIG. 3 is a lateral diagrammatic view of a laser interferometer useful in the invention.

Drawing FIGS. 1–3 illustrate this feature as configured in accordance with the known Michelson type of interferometer 50. A light beam 54 generated by a collimated light source 52 such as a laser is directed at a beamsplitting surface 56 of a beamsplitter 60. A first split beam 62 is reflected from the beamsplitting surface 56 to the wafer surface 22 and is reflected back to the beamsplitter 60, passing through it to a detector 70 as beam 64. A second split beam 66 passes through the beamsplitter 60 and anti-reflection surface 58 to a reflecting surface 68 an axially movable mirror 72, from which the beam 66 is reflected back to the beamsplitter 60. The reflected beam 66 is further reflected from the beamsplitting surface 56 and passes to the detector 70 as part of beam 64. Depending upon the difference in distance traveled by the first split beam 62 and by the second split beam 66, the two beam portions received as beam 64 by the detector 70 will interfere constructively or destructively. Compensating plate 74 compensates for the thickness of the beamsplitter 60, and may be unnecessary when the generated light beam 54 is monochromatic or quasi-monochromatic. In a preferred embodiment, the generated light beam 54 is a coherent laser beam.

The function of the beam splitter is to superimpose the mirror images onto each other and determine the phase difference and hence the difference in distance traveled by the first and second split beams 62, 66. The difference in traveled distance is twice the control distance 76. Sample distance 78 equals the total of control distance 76 and mirror distance 80. The detector 70 measures the change in amplitude of the beam 64 from which the difference in phase between beams 62 and 64 may be calculated and counts interference fringes. A warped wafer 24 will change the sample distance 78 and this change in distance relative to the mirror distance 80 (or the control distance 76) will be detected and quantified by the detector 70. Mirror controller 90 provides precise axial movement 88 of mirror 72, controlling distance 76 for determining the phase difference and may be used for phase modulation. Signal lines 82, 84, and 86 interconnect the light source 52, detector 70, mirror controller 90 and the controller/recorder/analyzer 40. Conductor 42 provides for vertical movement of stage 14, by which the stage controller 16 raises or lowers the wafer/die 24 to compensate for measured warpage or other source of non-planarity. Alternatively, the DC bias of the wafer/die 24 relative to the extraction plate 151 may varied, i.e., raised or lowered to maintain a constant extraction field.

Movement of the stage 14 by the stage controller 16 may be continuously controlled in each of the X, Y and Z axes, so that the primary ion beam 20 may be scanned and rastered over the desired X-Y sample area 98 and the ion gun may also be maintained at a relatively constant distance from the wafer surface 22. Thus, the surface 22 will be sputtered to a relatively constant depth 45, constant extraction field, and sputtering will be substantially confined to the oxide layer 44, which is a desired result of this method.

While a Michelson type of laser interferometer is illustrated in drawing FIGS. 1 and 3, the interferometer may alternatively be a "grazing incidence" interferometer of the Twyman-Green type or may be of another configuration, e.g., Mach-Zehnder, Shearing, or Fabry-Perot interferometer. Also, by further using phase modulation on the above-referenced interferometers, the absolute position of the wafer can be evaluated using well known Fourier transform calculations. The various types of interferometer generally differ in the beam geometries and in analytical treatment of the response. Incorporation of a particular type of interferometer into a SIMS or TOF-SIMS apparatus should be made with measurement accuracy and ease of operation in mind.

Placement of an interferometer in a mass spectrometer will require that the first split beam 62 be separated from the primary ion beam 20. This separation distance 92 may be e.g., about 0.5–2 cm. This problem may be overcome by initially scanning the wafer surface 22 with the interferometer 50, storing the planarity results, and providing continuous or semi-continuous correction during the sputtering operation. Alternatively, in situ remote interferometric measurements may be taken during the sputtering operations and corrections made based on calculated deviations from planarity.

Referring to drawing FIGS. 5 through 8, another type of interferometer, a "grazing incidence" interferometer 100 is illustrated for use in the present invention. By using a grazing incidence interferometer 100 and by using "phase modulation" techniques the basic data generated from scanning the surface of a wafer is readily transferred to a computer for analysis through the use of well-known Fourier series phase calculation techniques to determine the degree and direction the wafer is warped.

Figure 5:
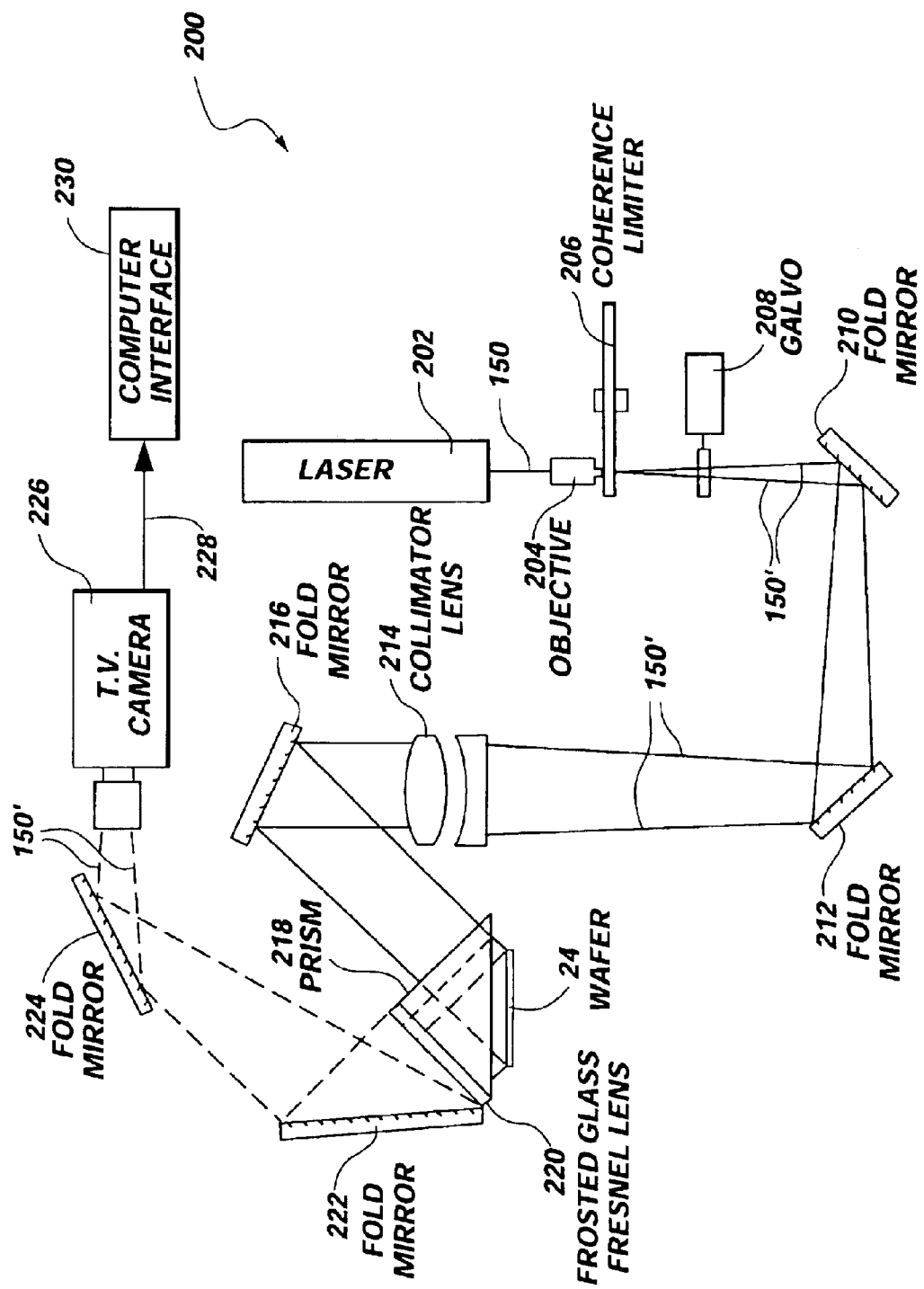
FIG. 5 is a side diagrammatic view of an alternative grazing angle interferometer used in the present invention.

As illustrated in drawing FIG. 5, the grazing incidence interferometer 200 typically includes a laser light source 202, objective 204, coherence limiter 206, GALVO 208, fold mirror 210, fold mirror 212, collimator lens 214, fold mirror 216, prism 218, fresnel lens 220, fold mirror 222, fold mirror 224, video (TV) camera 226, video output 228, and computer interface 230. Laser beam 150 is illustrated emanating from laser source 202, dividing into beams 150', which are received by video camera 226 after being reflected from the wafer 24 supported on a suitable member (not shown).

Figure 6:
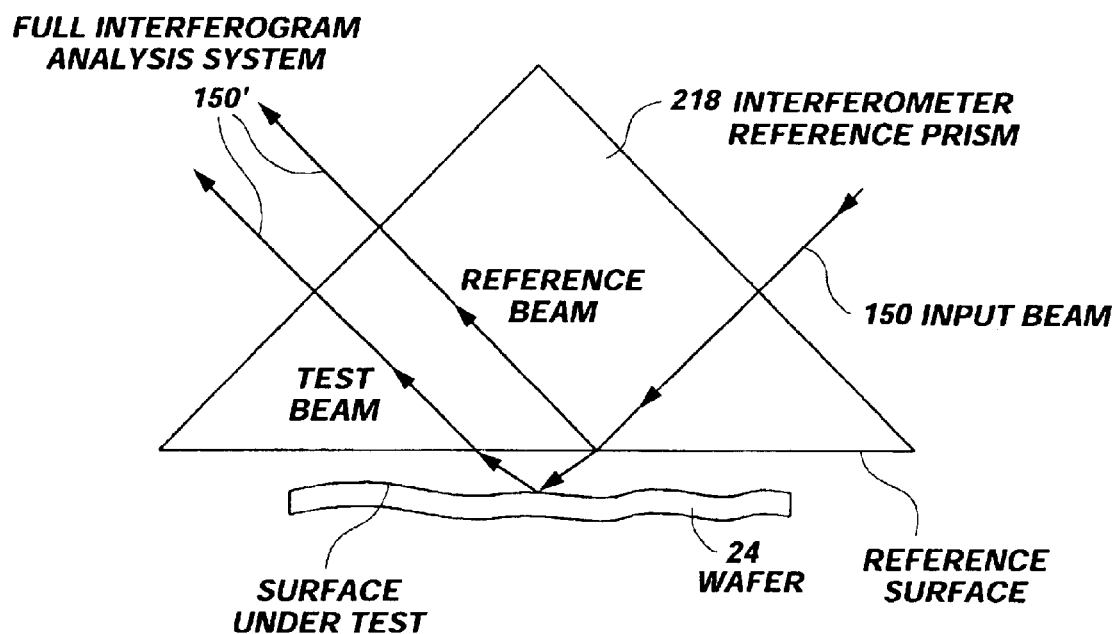
FIG. 6 is a graphical representation of the grazing property of the grazing angle interferometer used in the present invention.

Referring to drawing FIG. 6, graphically represented, a laser beam 150 is illustrated grazing off the surface of a wafer 24 at a relatively large angle to the surface normal through prism 218. Using this method of "grazing incidence" for the laser beam off the surface of the wafer and by using "phase modulation" techniques the basic data is readily transferred from the video camera (not shown) to the computer interface for analysis by the computer using Fourier series phase calculation techniques to determine the surface variations and direction of the surface variation. By striking a surface at a shallow angle with the laser beam, objects which are considered quite diffuse become near-perfect reflectors of the laser beam.

Figure 7:
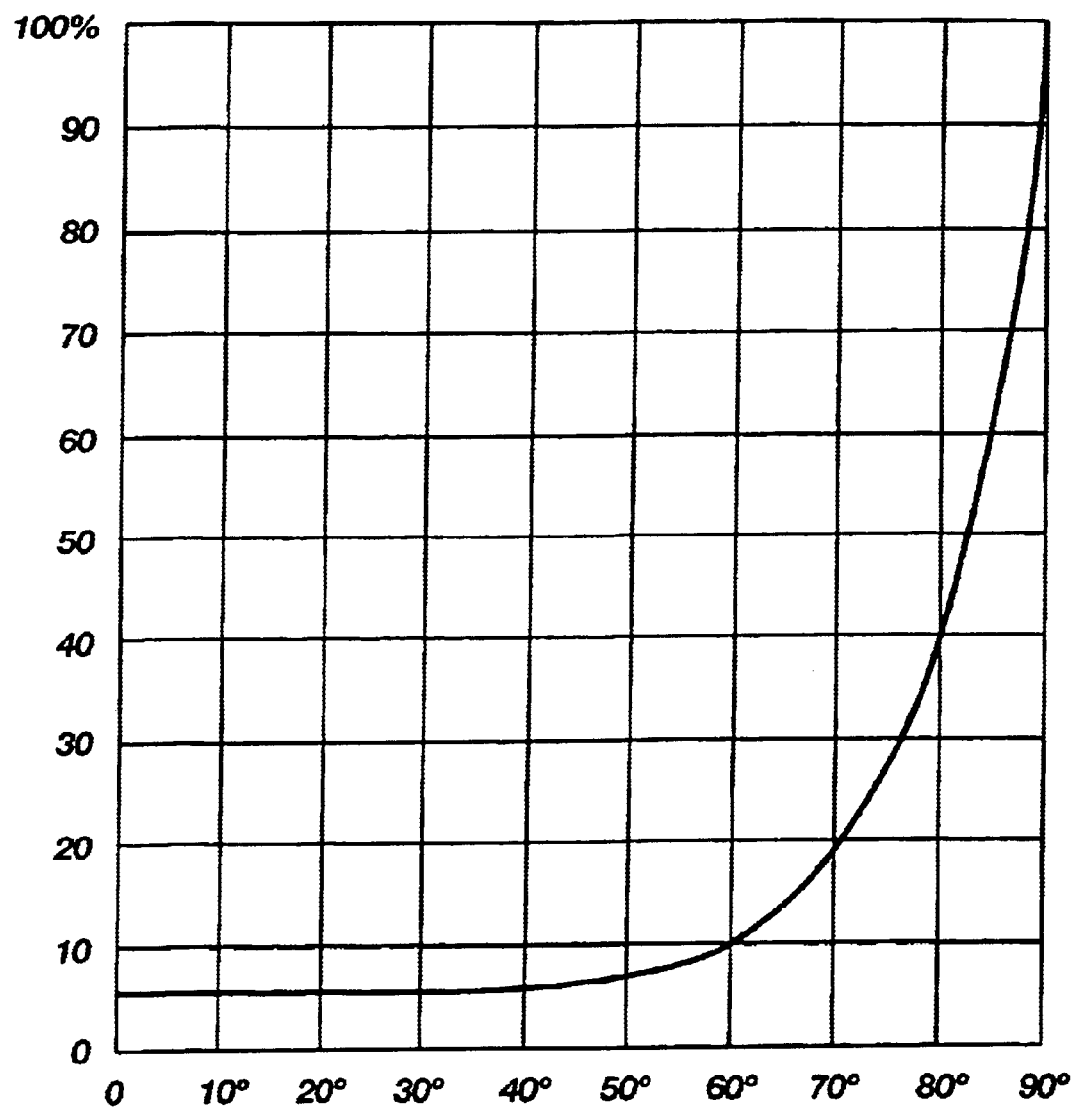
FIG. 7 is a graphical representation of the increase in reflection of the beam as the grazing incidence angle is increased.

Referring to drawing FIG. 7, illustrated is the increase in reflection as the angle of grazing incidence is increased.

Referring to drawing FIG. 8, illustrated in TABLE 1, are wafer surfaces of wafers of varying materials and associated wafer surface conditions for which grazing interferometers have been used to measure.

It will be evident to those skilled in the art that various changes and modifications may be made in the methods and apparatus as disclosed herein without departing from the spirit and scope of the invention as defined in the following claims.

What is claimed is:

1. A method for determining the concentration of a contaminant in a thin oxide surface layer having a depth, the thin oxide surface layer located on a semiconductor material, the method comprising:

providing a mass spectrometer apparatus having a primary sputtering ion beam, directing apparatus, and analyzing apparatus, the directing apparatus and analyzing apparatus for directing and analyzing a secondary ion stream produced by operation of the mass spectrometer apparatus, the mass spectrometer apparatus comprising one of a secondary ion mass spectrometer (SIMS) and a time-of-flight secondary ion mass spectrometer (TOF-SIMS);

predetermining a mass of surface layer required to be sampled for determining a contaminant concentration;

supporting the semiconductor material on a movable mechanical stage within the mass spectrometer apparatus;

moving the movable mechanical stage in a scanning motion while sputtering the thin oxide surface layer;

directing the secondary ion stream produced by operation of the mass spectrometer apparatus for analysis, the semiconductor material sputtered to a depth not generally exceeding the depth of the thin oxide surface layer;

moving the movable mechanical stage in a rastering motion to sputter and analyze the thin oxide surface layer over an extended area; and measuring a non-planarity of the thin oxide surface layer.

2. The method of claim 1, wherein the thin oxide surface layer is sputtered over an extended area comprising at least about $4 \times 10^4$ $\mu m^2$.

3. The method of claim 1, wherein the thin oxide surface layer is repetitively sputtered in multiple passes of increasing penetration, a total sputter penetration substantially not exceeding the depth of the thin oxide surface layer, and a sputtered secondary ion stream from each pass is separately analyzed to determine component analysis as a function of depth.

4. The method of claim 1, wherein a sputtering rate in mass per unit time is controlled by varying a strength of the primary sputtering ion beam and the sputter depth is controlled by varying a scanning speed in length per unit time.

5. The method of claim 1, further comprising:

continuously correcting for the non-planarity of the thin oxide surface layer during sputtering.

6. The method of claim 1, wherein measuring the non-planarity of the thin oxide surface layer comprises:

directing one portion of an interferometer split beam to an X-Y location on the thin oxide surface layer, the one portion being reflected back to a detector;

directing another portion of the interferometer split beam to a mirror at a known distance, the another portion being reflected back to the detector; and determining a difference in traveled distance using phase modulation and Fourier analysis for determining a thin oxide surface layer offset.

7. The method of claim 6, wherein measuring the non-planarity comprises:

moving the mechanical stage along a Z-axis to maintain an approximately constant distance between the primary sputtering ion beam of the mass spectrometer apparatus and the thin oxide surface layer being sputtered.

8. The method of claim 6, wherein measuring the non-planarity comprises:
changing an electrical potential of the thin oxide surface layer relative to an extraction potential.

9. A method for determining a concentration of a contaminant in a thin oxide surface layer having a depth, the thin oxide surface layer located on a semiconductor material, the method comprising:
providing a mass spectrometer apparatus having a primary sputtering ion beam, a directing apparatus, and an analyzing apparatus, the directing apparatus and analyzing apparatus for directing and analyzing the secondary ion stream produced by operation of the mass spectrometer apparatus, the mass spectrometer apparatus comprising one of a secondary ion mass spectrometer (SIMS) and a time-of-flight secondary ion mass spectrometer (TOF-SIMS);
predetermining a mass of surface layer required to be sampled for determining a contaminant concentration at preset limits of the contaminant concentration;
supporting the semiconductor material on a movable mechanical stage within the mass spectrometer apparatus;
moving the movable mechanical stage while sputtering the thin oxide surface layer;
directing the secondary ion stream to the mass spectrometer apparatus for analysis, the movable mechanical stage moved at a speed, the semiconductor material sputtered to a depth not substantially exceeding the depth of the thin oxide surface layer;
moving the movable mechanical stage in a rastering motion to sputter and analyze the thin oxide surface layer over an extended area, a total sputtered analyte approximately equaling the predetermined required mass of surface layer; and
measuring a non-planarity of the thin oxide surface layer.

10. The method of claim 9, wherein the thin oxide surface layer is sputtered over an extended area comprising at least about $4 \times 10^4$ $\mu m^2$.

11. The method of claim 9, wherein the thin oxide surface layer is repetitively sputtered in multiple passes of increasing penetration, whereby a total sputter penetration does not generally exceed the depth of the thin oxide surface layer and a sputtered secondary ion stream from each pass is separately analyzed to determine component analysis as a function of depth.

12. The method of claim 9, wherein a sputtering rate in mass per unit time is controlled by varying a strength of the primary sputtering ion beam and the sputter depth is controlled by varying a scanning speed in length per unit time.

13. The method of claim 9, further comprising:
continuously correcting for the non-planarity of the thin oxide surface layer during sputtering.

14. The method of claim 13, wherein measuring the non-planarity of the thin oxide surface layer comprises:
directing one portion of an interferometer split beam to an X-Y location on the thin oxide surface layer whereby the one portion is reflected back to a detector;
directing another portion of the interferometer split beam to a mirror at a known distance and using phase modulation, the another portion being reflected back to the detector; and
determining a difference in traveled distance using Fourier analysis.

15. The method of claim 13, wherein measuring the non-planarity comprises:
moving the mechanical stage along a Z-axis to maintain an approximately constant distance between a source of the primary sputtering ion beam and the thin oxide surface layer being sputtered.

16. The method of claim 13, wherein measuring the non-planarity comprises:
changing an electrical potential of the thin oxide surface layer relative to an extraction potential.

17. An apparatus for determining quantities of conductive trace elements and compounds in a shallow surface layer having a depth, the apparatus comprising:
a movable mechanical stage configured to move a semiconductor wafer laterally in X and Y axes and at least one other axis;
a primary ion beam for focusing on a shallow surface layer of the semiconductor wafer;
a mass spectrometer detector and analyzer configured to determine a content of a secondary ion stream, the mass spectrometer detector comprising one of a SIMS and a TOF-SIMS;
directing apparatus configured to direct the secondary ion stream to the mass spectrometer detector for analysis; and
stage control apparatus configured to move the movable mechanical stage at a planar scanning speed in multiple scanning paths such that the primary ion beam is rastered over an area not confined to electrostatically rasterable area limits.

18. The apparatus of claim 17, wherein the movable mechanical stage comprises a stage movable in lateral X and Y axes and in a vertical Z axis.

19. The apparatus of claim 17, further comprising:
planarity determining apparatus for determining non-planarity of the shallow surface layer along the multiple scanning paths and providing correction for the non-planarity.

20. An apparatus for determining concentrations of trace components of a surface layer having a depth on a semiconductor wafer, the apparatus comprising:
a secondary ion mass spectrometer having a primary sputtering beam for producing a secondary ion stream and a secondary ion detector to receive the secondary ion stream, the secondary ion mass spectrometer comprising one of a SIMS and a TOF-SIMS;
a movable stage configured to support, scan and raster the surface layer of the semiconductor wafer to produce the secondary ion stream, the movable stage movable in at least two axes of direction;
an interferometer to determine non-planarity of the surface layer; and
control apparatus for providing a uniform extraction field of the surface layer depth independent of the non-planarity of the surface layer.

* * * * *

UNITED STATES PATENT AND TRADEMARK OFFICE
CERTIFICATE OF CORRECTION

PATENT NO. : 6,855,928 B2  Page 1 of 1
APPLICATION NO. : 10/358939
DATED : February 15, 2005
INVENTOR(S) : Eugene P. Marsh It is certified that error appears in the above-identified patent and that said Letters Patent is hereby corrected as shown below:

On the title page:
In ITEM (56) "References Cited,
U.S. Patent Documents,"   insert --6,107,629   08/22/00   Benninghoven et al.--

| | | |
|---|---|---|
| COLUMN 4, | LINE 4, | change "spectometer" to --spectrometer-- |
| COLUMN 4, | LINE 57, | change "in situ" to --*in situ*-- |
| COLUMN 5, | LINE 5, | after "FIG 1." and before "front" insert --is a-- |
| COLUMN 6, | LINE 1, | change "mastering" to --rastering-- |
| COLUMN 9, | LINE 39, | change "laser source 202" to --laser light source 202-- |

Signed and Sealed this

Fourth Day of December, 2007

JON W. DUDAS
*Director of the United States Patent and Trademark Office*